(12) United States Patent
Tsuri

(10) Patent No.: US 9,675,241 B2
(45) Date of Patent: Jun. 13, 2017

(54) OPHTHALMIC EXAMINATION APPARATUS AND OPHTHALMIC EXAMINATION SYSTEM

(71) Applicant: KABUSHIKI KAISHA TOPCON, Itabashi-ku (JP)

(72) Inventor: Shigetaka Tsuri, Itabashi-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 15/077,202

(22) Filed: Mar. 22, 2016

(65) Prior Publication Data

US 2016/0360958 A1  Dec. 15, 2016

(30) Foreign Application Priority Data

Jun. 9, 2015 (JP) ................................ 2015-116947

(51) Int. Cl.
*A61B 3/14* (2006.01)
*A61B 3/10* (2006.01)
*A61B 3/00* (2006.01)
*A61B 5/00* (2006.01)

(52) U.S. Cl.
CPC ............ *A61B 3/0025* (2013.01); *A61B 3/102* (2013.01); *A61B 3/14* (2013.01); *A61B 5/7275* (2013.01)

(58) Field of Classification Search
USPC ................................................. 351/200–246
See application file for complete search history.

(56) References Cited

U.S. PATENT DOCUMENTS

| | | | |
|---|---|---|---|
| 2012/0121158 A1 | 5/2012 | Sekine et al. | |
| 2013/0286349 A1* | 10/2013 | Iwanaga | A61B 3/14 351/206 |
| 2014/0016096 A1* | 1/2014 | Iwase | A61B 3/0025 351/206 |
| 2014/0028975 A1* | 1/2014 | Takai | A61B 3/102 351/206 |
| 2014/0063460 A1* | 3/2014 | Borycki | A61B 3/102 351/208 |
| 2014/0078466 A1 | 3/2014 | Sekine et al. | |
| 2015/0085252 A1 | 3/2015 | Fujimura et al. | |

FOREIGN PATENT DOCUMENTS

| | | |
|---|---|---|
| JP | 2011-24930 | 2/2011 |
| JP | 2013-248376 | 12/2013 |
| JP | 2015-35111 | 2/2015 |

* cited by examiner

*Primary Examiner* — Mohammed Hasan
(74) *Attorney, Agent, or Firm* — Oblon, McClelland, Maier & Neustadt, L.L.P.

(57) ABSTRACT

According to one embodiment, an ophthalmic examination apparatus includes an examination unit and an analyzer. The examination unit is used to optically examine a subject's eye. The analyzer is configured to analyze examination data obtained by the examination unit, and thereby generate risk information indicating the risk of a specific disease.

8 Claims, 8 Drawing Sheets

FIG. 5A

| | EXAMINATION ITEM a | EXAMINATION ITEM b | EXAMINATION ITEM c | ... |
|---|---|---|---|---|
| DISEASE A | ○ | — | — | ... |
| DISEASE B | ○ | — | ○ | ... |
| DISEASE C | — | ○ | ○ | ... |
| ... | ... | ... | ... | ... |
| ... | ... | ... | ... | ... |

| | | EXAMINATION ITEM a | EXAMINATION ITEM b | EXAMINATION ITEM c | ... |
|---|---|---|---|---|---|
| DISEASE A | RISK HIGH | ○ | ○ | | ... |
| | RISK MEDIUM | ○ | | ... | ... |
| | RISK LOW | ○ | ○ | ○ | ... |
| DISEASE B | RISK HIGH | ○ | ... | ○ | ... |
| | RISK MEDIUM | ○ | ○ | ○ | ... |
| | RISK LOW | ... | ... | ○ | ... |
| DISEASE C | RISK HIGH | ... | ○ | ○ | ... |
| | RISK MEDIUM | ... | ○ | ... | ... |
| | RISK LOW | ... | ... | ... | ... |
| ... | ... | ... | ... | ... | ... |

462

OPHTHALMIC EXAMINATION APPARATUS AND OPHTHALMIC EXAMINATION SYSTEM

CROSS-REFERENCE TO RELATED APPLICATION

This application is based upon and claims the benefit of priority from Japanese Patent Application No. 2015-116947, filed Sep. 6, 2015; the entire contents of which are incorporated herein by reference.

FIELD

Embodiments described herein relate generally to an ophthalmic examination apparatus and an ophthalmic examination system.

BACKGROUND

Human beings perceive external information through five senses (sight, hearing, smell, taste, and touch), and more than 80 percent of it comes via the sense of sight. Therefore, the health of the vision is very important in order to maintain and improve the quality of life (QOL). Meanwhile, along with the aging of the population, there have been an increasing number of potential patients with eye diseases such as glaucoma, diabetic retinopathy, and age-related macular degeneration. This trend is assumed to further intensify. There is a need for early detection and prognostic control by screening to identify such potential patients to thereby maintain and improve QOL.

The screening of eye diseases is carried out with a variety of ophthalmic examination apparatuses. In particular, for patients with early disease before the subjective symptoms appear, an apparatus for understanding the eye's form and function is considered to be effective. Fundus cameras and scanning laser ophthalmoscopes (SLO) have been used as an apparatus of this kind. In recent years, an optical coherence tomography is used in addition to or in place of such a conventional apparatus.

The optical coherence tomography (OCT) provides a high-definition image (two-dimensional cross sectional image, three-dimensional image, enface image, etc.) of an ocular tissue (retina, choroid, lamina cribrosa, cornea, corner, etc.). By analyzing data obtained by the optical coherence tomography, the form (shape, thickness, area, volume, position, distribution, etc.) of a site of interest (tissue, lesion, etc.) can be obtained. Besides, there are technologies for determining the presence or risk of the eye disease by a comparison between the analysis data thus obtained and the database of normal eyes, and they have been put into practical use. Further, the optical coherence tomography is also used to measure the function such as the dynamics of blood and intraocular fluid.

In addition to being capable of acquiring the internal morphology of the eye tissue with high precision, the optical coherence tomography has various advantages in screening including, for example, that examination requires less time, the examination is performed without contact, and the examination can be performed even for an eye with a cataract or a small pupil. Further, the operability of the optical coherence tomography has been improved due to the automation of the alignment of its optical system with the eye, the automation (operation mode) of a series of actions for examination, or the like. Thus, even an unskilled person can easily conduct an examination.

It has been found that a sign of a disease other than eye diseases can be detected by ophthalmic examination. For example, there have been reports about the detection of early lesions of diseases such as diabetes, cancer, Alzheimer's disease, hypertension, arteriosclerosis, and the like. Generally, the screening of such diseases is performed by using an X-rays diagnostic apparatus, an X-ray CT apparatus, a positron emission tomography (PET) apparatus, a single photon emission computed tomography (SPECT) apparatus, a magnetic resonance imaging (MRI) apparatus, or the like. However, these modalities involve drawbacks such as radiation exposure, long examination time, and high costs. This makes it difficult to broadly offer the screening.

For example, Japanese Unexamined Patent Application Publication Nos. 2011-24930, 2013-248376, and 2015-35111 disclose the conventional technologies.

SUMMARY

Embodiments are intended to provide an apparatus and a system capable of broadly offering the screening of various diseases through an ophthalmic examination.

According to one embodiment, an ophthalmic examination apparatus includes an examination unit and an analyzer. The examination unit is used to optically examine a subject's eye. The analyzer is configured to analyze examination data obtained by the examination unit, and thereby generate risk information indicating the risk of a specific disease.

BRIEF DESCRIPTION OF THE DRAWINGS

FIG. 5A is a schematic diagram illustrating an example of a configuration according to an embodiment;

FIG. 5B is a schematic diagram illustrating an example of a configuration according to an embodiment;

DETAILED DESCRIPTION

Figure 1:
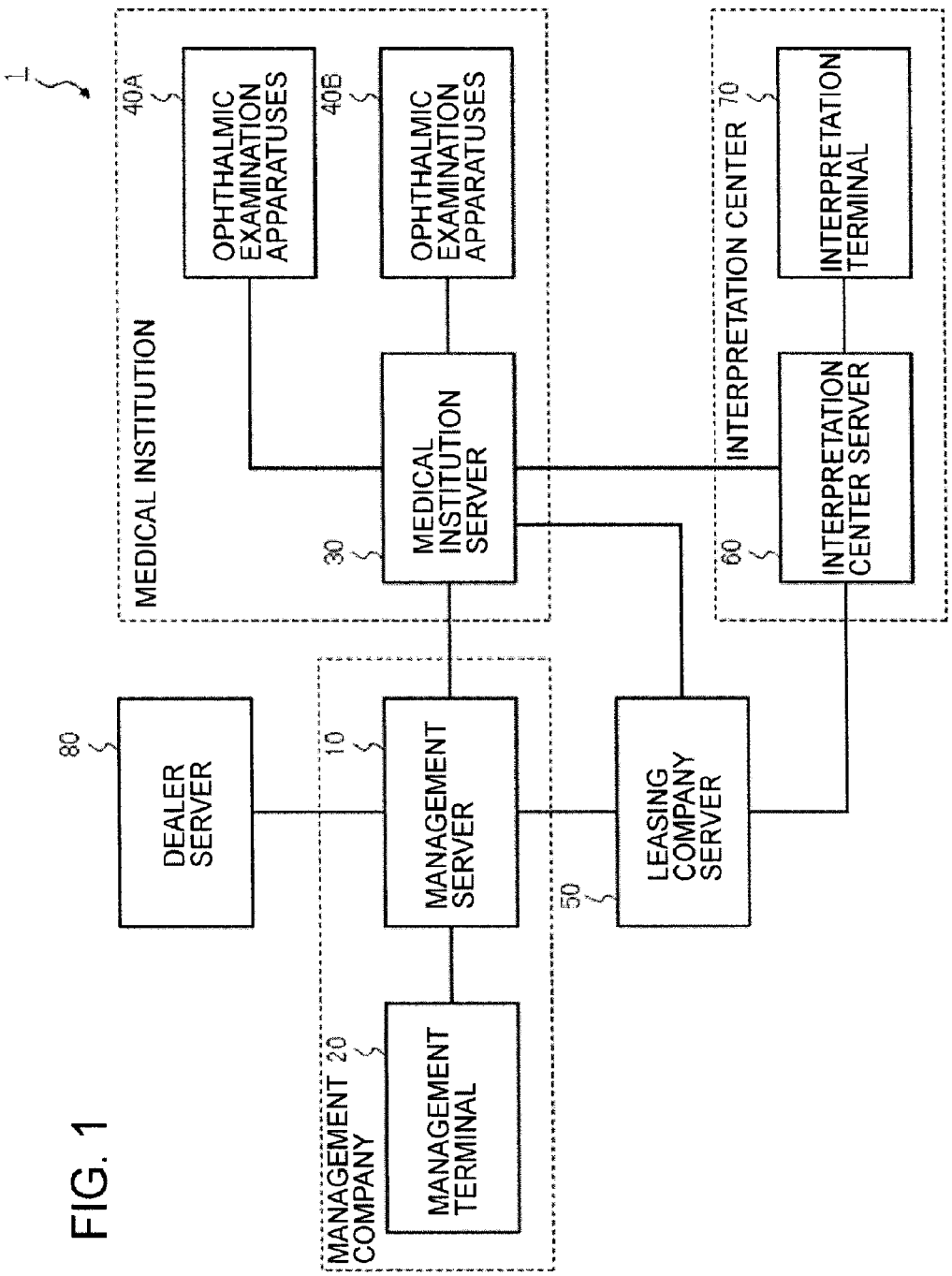
FIG. 1 is a schematic diagram illustrating an example of a configuration according to an embodiment.

Referring now to the drawings, the present invention is described through some exemplary embodiments. Any content of the documents cited in the specification can be incorporated herein by reference.

<System Configuration>

A system according to an embodiment is used to broadly carry out the screening of one or more diseases. The screening of diseases is used in, for example, health diagnosis and health check. Examination for screening is performed by using a plurality of ophthalmic examination apparatuses installed in a plurality of medical institutions. One or more types of ophthalmic examination apparatuses (typically, optical coherence tomography) are used for the examination for screening.

FIG. 1 illustrates an example of an ophthalmic examination system 1 according to an embodiment. A management company, a leasing company and an interpretation center are involved in the service provided by the ophthalmic examination system 1 illustrated in FIG. 1. The service is provided to a plurality of medical institutions. One or more ophthalmic examination apparatuses are installed in each of the medical institutions. The management company is, for example, the manufacturer of the ophthalmic examination apparatus, or an organization that has been entrusted with the management from the manufacturer or the like. A dealer is a business entity (company) which promotes the service to the medical institutions.

If a medical institution enters into a contract for the service, contract details and information about the medical institution are sent from an information processing equipment installed in the dealer (a dealer server 80) to an information processing equipment (a management server 10) installed in the management company. The contract details include the type and number of ophthalmic examination apparatuses to be installed. The staff of the management company checks the information sent from the medical institution with the information processing equipment (a management terminal 20) connected to the management server 10 via a network such as LAN. The management company (the manufacturer of the ophthalmic examination apparatus) sells the ophthalmic examination apparatuses of the type as many as the number indicated in the contract to the leasing company. The leasing company rents (leases) the purchased ophthalmic examination apparatuses to the medical institution.

Incidentally, the ophthalmic examination apparatus used in the service may offer improved operability with automatic alignment and operation mode (screening mode). Thus, if the user is inexperienced in the use of the ophthalmic examination apparatus, he/she can carry out examination easily. Even the subject can perform examination by operating the ophthalmic examination apparatus. Such an ophthalmic examination apparatus enables not only the wide provision of the screening of eye disease but also the wide provision of the screening of any disease that involves a change in the form and/or function of the eye.

After the installation of the ophthalmic examination apparatuses, the service is started to be provided to the medical institution. Data of an eye obtained by the ophthalmic examination apparatuses is sent to an examination result analysis institution such as an interpretation center. In the example of FIG. 1, data (image, etc.) acquired by ophthalmic examination apparatuses 40A and 40B is sent from the information processing equipment (a medical institution server 30) installed in the medical institution to an information processing equipment (an interpretation center server 60) installed in the interpretation center. A radiologist makes an interpretation of the image received from the medical institution by using an information processing equipment (an interpretation terminal 70) connected to the interpretation center server 60 via a network such as LAN or the like, and creates an interpretation report. The interpretation report thus created is sent from the interpretation center server 60 to the medical institution server 30. A doctor in the medical institution creates a report based on the interpretation report, other examination results, diagnosis results, and the like. Examples of the report include electronic medical record, health diagnostic report, and examination report. Thus, even if the doctor is not a specialist in ophthalmology, he/she can create a report based on the diagnosis results made by the ophthalmologist (radiologist). Further, the medical institution can carry out the screening of eye diseases as well as the screening of diseases other than the eye diseases.

To spread the service, it is desirable to reduce the costs and risks involved in introducing the service. To that end, in this system, the medical institution rents (leases) the ophthalmic examination apparatuses instead of purchasing them. Further, it is possible to adopt a usage-based billing in addition to the regular billing (e.g. certain monthly fee). On a pay-per-use basis, the billing is made, for example, based on the number of times of use (use count) of the ophthalmic examination apparatus. For this purpose, there is a need for a technology to count the number of uses of the ophthalmic examination apparatus.

On the other hand, the medical fees that the medical institution charges to the subject (patient) are not proportional to the use count of the ophthalmic examination apparatus in general. For example, regardless of whether one or both eyes are examined with the ophthalmic examination apparatus, the amount of the medical fees (medical fee points) for the examination does not change. The same applies if the examination is performed again. Further, even when the same subject is examined on different days, if both the examination dates are within a predetermined period of time (e.g., one month), medical fees for only a single examination may be charged.

In this manner, it is desirable that the "use count" take into account the payment system for medical services rather than the number of times the ophthalmic examination apparatus has been actually operated (the number of examinations). In other words, it is desirable to design a charging scheme in consideration of the payment system for medical services, and also define the "use count", which is the basis of charge, in this way. Described below is an example of such a system which is constructed in view of the foregoing.

<Embodiment for Counting the Number of Uses of the Ophthalmic Examination Apparatus>

Figure 2:
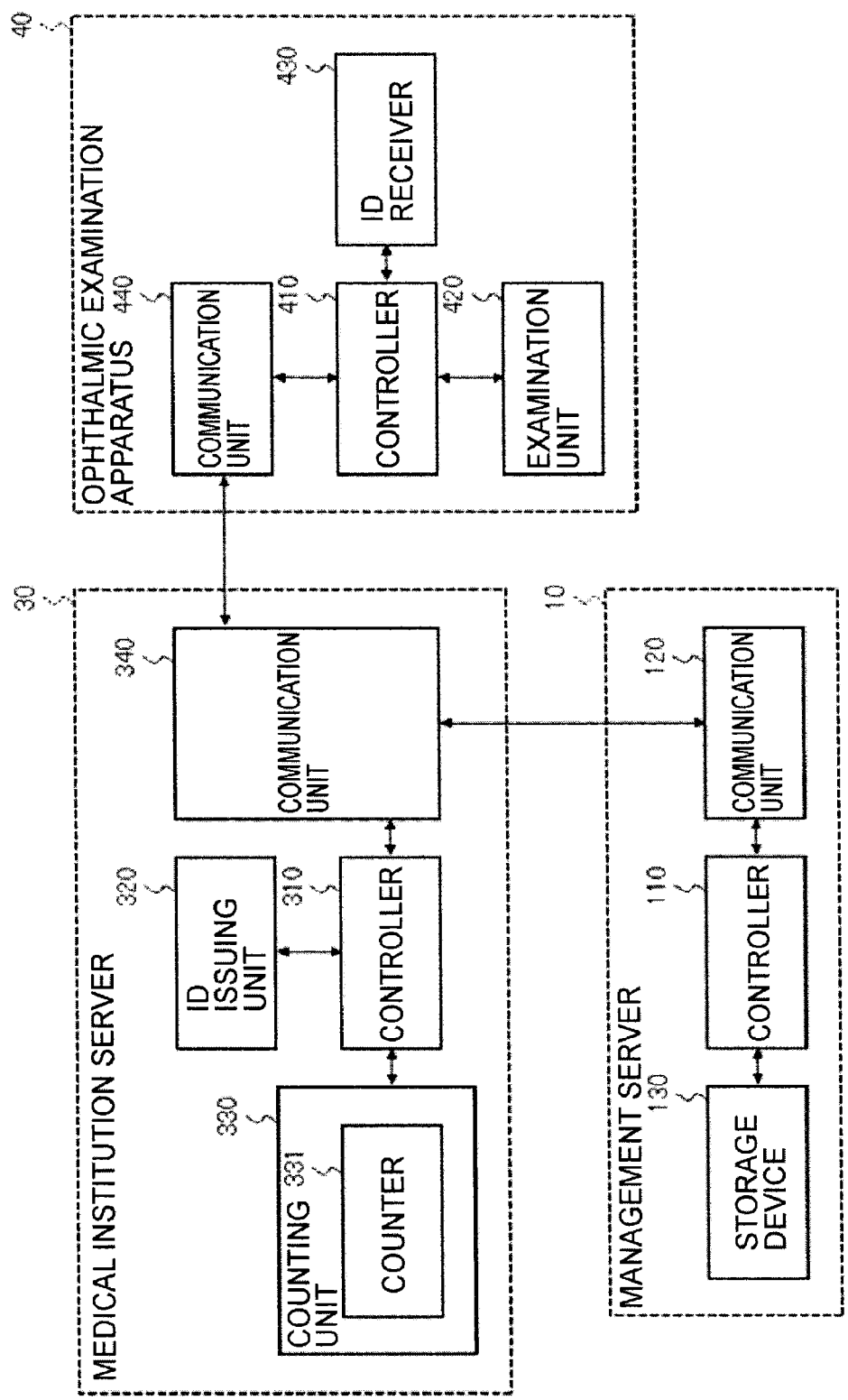
FIG. 2 is a schematic diagram illustrating an example of a configuration according to an embodiment.

FIG. 2 illustrates an example of a configuration for providing a function of counting the number of uses of the ophthalmic examination apparatus according to an embodiment. As illustrated in FIG. 2, the configuration includes the management server 10, the medical institution server 30, and the ophthalmic examination apparatus 40. The ophthalmic examination apparatus 40 represents either one of the ophthalmic examination apparatuses 40A and 40B illustrated in FIG. 1. One or more ophthalmic examination apparatuses are installed in the medical institution. Each ophthalmic examination apparatus has the configuration as illustrated in FIG. 2. In the following, the ophthalmic examination apparatus 40, the medical institution server 30, and the management server 10 are described in this order.

<Ophthalmic Examination Apparatus 40>

The ophthalmic examination apparatus 40 is any device used for the examination of an eye, and may be, for example, a device capable of performing optical coherence tomography. The ophthalmic examination apparatus 40 includes a controller 410, an examination unit 420, an ID receiver 430, and a communication unit 440.

The controller 410 controls each unit of the ophthalmic examination apparatus 40. The controller 410 includes a processor. Further, the controller 410 includes a storage device such as RAM, ROM, a hard disk drive, and a solid state drive. The ROM, the hard disk drive or the solid state drive stores computer programs to execute control operations. The processor loads the computer programs into the RAM and executes them to perform the control operations. The storage device stores identification information of the ophthalmic examination apparatus 40 (apparatus ID) in advance.

The examination unit 420 has a known structure for generating examination data by optically examining the subject's eye. If the examination unit 420 has the function of performing optical coherence tomography (OCT unit), the OCT unit includes a light source, an interference optical system, and a data processor. The interference optical system splits light from the light source into measurement light and reference light, and guides the measurement light onto the subject's eye. Besides, the interference optical system superposes return light of the measurement light returning from the subject's eye on the reference light to generate interference light, and detects it. An optical scanner is provided on the optical path of the measurement light to sequentially deflect the measurement light according to a preset pattern. This implements the OCT scan of the eye. The data processor applies processing such as noise removal (noise reduction), filtering, dispersion compensation, fast Fourier transform (FFT), and the like to the detection result of the interference light (detection signal), thereby generating a one-dimensional image (A-scan image) extending in the depth direction (axial direction). Further, the data processor arranges a plurality of A-scan images obtained by the OCT scan according to a preset pattern to obtain an image representing a two-dimensional cross section extending in the depth direction and the scanning direction (B-scan image), a three-dimensional image, and the like. By slicing the three-dimensional image, an image representing a cross section perpendicular to the depth direction (C-scan image), an image of any cross section (MPR image), and the like can be obtained. The examination unit 420 may be provided with a function of analyzing data acquired by the optical examination.

The OCT unit has a configuration corresponding to the type of OCT. In a typical example of a case where spectral-domain OCT is applied, the light source is a low-coherence light source (broad-band light source), and the interference optical system detects the interference light by a spectroscope. Meanwhile, in a typical example of a case where swept-source OCT is applied, the light source is a wavelength swept light source (wavelength tunable light source), and the interference optical system detects the interference light by a balanced photodiode.

The ID receiver 430 receives identification information of the subject (subject ID) to be examined by the ophthalmic examination apparatus 40. Examples of the subject ID include ID assigned to each patient in a hospital and ID issued in a medical examination center or a screening venue. The ID receiver 430 includes, for example, hardware keys and/or software keys operated to manually enter the subject ID. The ID receiver 430 may further include a data reader for reading the subject ID recorded on an IC card, a magnetic card, or the like. In addition, the ID receiver 430 may include a data reader for reading an identifier such as a bar code printed on paper. The subject ID received by the ID receiver 430 is sent to the controller 410.

The communication unit 440 communicates with other devices via a communication line, cable, or the like by an arbitrary communication system. For example, the communication unit 440 includes a communication interface conforming to the Internet, a communication interface conforming to LAN, a communication interface conforming to near field communication, and the like. Data sent and received by the communication unit 440 may be encrypted. In that case, the ophthalmic examination apparatus 40 (e.g. the controller 410) includes an encryptor that encrypts transmission data, and a decoder that decodes received data.

<Medical Institution Server 30>

The medical institution server 30 is an information processing equipment for processing and managing various types of information in the medical institution. The medical institution server 30 has at least a function of performing processes of the embodiment, and may further have any other function. The medical institution server 30 includes one or more information processing equipments. The medical institution server 30 may have a database function to manage information stored in a mass storage device.

Although not illustrated, in the medical institution, a variety of information processing equipments and information processing systems capable of communicating with the medical institution server 30 are used. Examples of the information processing equipments and the information processing systems include: a doctor terminal used by a doctor; an electronic medical record system to store and manage electronic medical records; an image management system to store and manage medical images, such as a picture archiving and communication system (PACS), an ophthalmic image management system, and the like; a receipt system to store and manage information related to medical fees; an interpretation terminal for interpreting medical images; and the like.

The medical institution server 30 includes a controller 310, an ID issuing unit 320, a counting unit 330, and a communication unit 340.

The controller 310 controls each unit of the medical institution server 30. The controller 310 includes a processor and a storage device. The processor performs control operations according to a computer program stored in the storage device.

The ID issuing unit 320 issues the subject ID. If the medical institution is a hospital, the ID issuing unit 320 issues a patient ID at the time of registration of a new patient.

In a medical examination center and a screening venue, generally, numerical values such as, for example, "0001", "0002", "0003", . . . are assigned to subjects of the day in the order of registration or attendance. In this case, the same number is assigned to different subjects who undergo a medical examination or the like on different days. The ID issuing unit 320 can add another identifier in order to avoid such duplication of identification information. For example, the ID issuing unit 320 is configured to add a character string that indicates the date of the medical examination or the like to the numerical value assigned to the subjects as described above. For example, if the examination date is "DD/MM/20YY" (day, month, year), the ID issuing unit 320 assigns subject IDs "0001-20YYMMDD", "0002-20YYMMDD", "0003-20YYMMDD", . . . to subjects of the day in the order of attendance. Thus, the uniqueness of the subject ID is ensured. The subject ID issued by the ID issuing unit 320 is sent to the controller 310.

The ID issuing unit 320 includes a processor and a storage device. The processor performs the process of ID issuance according to a computer program stored in the storage device.

The counting unit 330 counts the number of uses of the ophthalmic examination apparatuses installed in the medical institution. In this embodiment, the counting unit 330 counts the number of uses of each of the ophthalmic examination apparatuses 40. Incidentally, the counting unit 330 may be configured to count the number of uses of a predetermined group including two or more ophthalmic examination apparatuses 40 (described later in "Modification"). The counting unit 330 includes a processor and a storage device. The processor performs a counting process as illustrated below according to a computer program stored in the storage device.

The counting unit 330 of the embodiment includes a counter 331 that indicates the number of uses of (each) ophthalmic examination apparatus 40 up to this time. If there are two apparatuses, i.e., the ophthalmic examination apparatuses 40A and 40B, as illustrated in FIG. 1, the counter 331 includes a "counter A" indicating the number of uses of the ophthalmic examination apparatus 40A up to this time, and a "counter B" indicating the number of uses of the ophthalmic examination apparatus 40B up to this time.

Each counter is reset to the initial value (that is, zero) at a predetermined timing. For example, when the management server 10 is notified of the number of uses indicated by the counter 331, the counting unit 330 resets the counter 331. The notification of the use count is described later. Besides, the counting unit 330 may be configured to record the use count in association with timing information upon resetting the counter 331. Examples of the timing information include the date and time at which the counter 331 is reset. With this, the history of the use count of the ophthalmic examination apparatus 40 is accumulated.

Described below is an example of the process to increment the value of the counter 331. The counter 331 is configured to increase the value by one unit. The one unit is, for example, "1". In this case, the value of the counter 331 is equal to the number of times of use. On the other hand, even if any value other than "1" is set as the one unit, the number of uses can be obtained based on the value set as the one unit. For example, if one unit is "0.1", the counter value "5" corresponds to the number of uses "50 times".

The first example is described below. One subject may be examined by the ophthalmic examination apparatus 40 a plurality of times within a predetermined time period (e.g., one month). In such circumstances, there is a case that it is allowed to charge medical fees for only one examination. In such cases, when one subject (i.e., a subject corresponding to a single subject ID) is examined for first time in a predetermined period, the counting unit 330 increases the counter value corresponding to the ophthalmic examination apparatus 40 by one unit. Thereafter, if the same examination is performed again within the predetermined period, the counting unit 330 leaves the counter value unchanged. With such a configuration, even if the same examination is performed a plurality of times within a predetermined time period, only the first examination can be counted.

To implement this, for example, the counting unit 330 includes a timer (timer, calendar, etc.) for recognizing the start and end of the predetermined time period. The counting unit 330 further includes a subject ID recorder that records the subject ID of a subject examined by the ophthalmic examination apparatus 40. The subject ID recorder is provided for each of the ophthalmic examination apparatuses 40 (i.e., each apparatus ID) or each type of examination (that is, each group of apparatus IDs). The timer and the subject ID recorder are reset each time the predetermined time period has elapsed. When the examination is performed by using the ophthalmic examination apparatus 40, the ID receiver 430 receives the subject ID of the subject. When the examination is completed, the controller 410 associates the subject ID, the apparatus ID of the ophthalmic examination apparatus 40, and examination data with one another, and sends them to the medical institution server 30. The counting unit 330 records the subject ID on the subject ID recorder corresponding to the apparatus ID. With this, the subject IDs of the subjects who undergo the examination within a predetermined time period are accumulated. When a new examination is performed by the ophthalmic examination apparatus 40, the counting unit 330 determines whether the subject ID, which is newly entered, is recorded on the subject ID recorder. If the new subject ID is not recorded, the counting unit 330 increases the counter corresponding to the ophthalmic examination apparatus 40 by one unit. On the other hand, if the new subject ID has already been recorded, the counting unit 330 leaves the value of the counter corresponding to the ophthalmic examination apparatus 40 unchanged. Thus, the process of the first example can be implemented.

The second example is described next. The examination may be performed for only one eye or both eyes of a subject. In such circumstances, there is a case that the same medical fees are charged for the examination of only one eye and the examination of both eyes. In such cases, regardless of whether the examination is performed for one eye (left or right eye) or both eyes (left and right eyes) of one subject (i.e., a subject corresponding to a single subject ID), the counting unit 330 increases the value of the counter, by one unit, corresponding to an apparatus group including the ophthalmic examination apparatus used for the examination.

To implement this, for example, having received the subject ID and the apparatus ID entered to the medical institution server 30 from the ophthalmic examination apparatus 40 together with examination data, the counting unit 330 increases the counter corresponding to the apparatus ID by one unit.

The third example is described. When the examination is not performed properly, or the like, re-examination is performed. In general, re-examination does not incur additional fees. The following configuration may be applied to deal with such cases. First, when one eye or both eyes of one subject (i.e., a subject corresponding to a single subject ID) is/are examined, the counting unit 330 increases the value of the counter corresponds to the ophthalmic examination apparatus 40 by one unit. Thereafter, when the eye(s) of the subject is examined again by using the ophthalmic examination apparatus 40, the counting unit 330 leaves the value of the counter unchanged.

This may be implemented by, for example, the same configuration as the first example. Further, in this example, the above process may be applied to the re-examination of the same eye or the re-examination of the same subject. The latter includes a case in which the examination of the different eye (the fellow eye) as well as the re-examination of the same eye).

In the latter case, reference to only the subject ID may suffice, as described above. On the other hand, in the former case, it is required to refer to information (subject's eye information) to identify the eye that has been examined (the left eye, the right eye, or the both eyes). The subject's eye information may be obtained from, for example, the operation mode of the ophthalmic examination apparatus 40 (e.g., both eyes examination mode, left eye examination mode, right eye examination mode, etc.). Further, if the ophthalmic examination apparatus 40 is configured to move the optical system in the lateral direction to examine the left and right subject's eyes, the subject's eye information may be generated based on the position(s) of the optical system at the time of the examination. In addition, when the ophthalmic examination apparatus 40 can capture an image of the subject's eye (e.g., when examination data includes the image of the subject's eye), the subject's eye information can be generated by analyzing the image.

The communication unit 340 communicates with other apparatuses via a communication line, a cable, or the like by an arbitrary communication system. For example, the communication unit 340 includes, for example, a communication interface compatible with the Internet, a communication interface compatible with LAN, and a communication interface compatible with near field communication. Data that the communication unit 340 transmits and receives may be encrypted. In this case, the medical institution server 30 (e.g. the controller 310) includes an encryptor that encrypts transmission data and a decoder that decodes received data.

The controller 310 controls the communication unit 340 to transmit the counter value indicated by the counter 331 to the management server 10. This is performed at a predetermined timing. Besides, the controller 310 associates the value indicated by each counter included in the counter 331 and an apparatus ID (the identification information of the ophthalmic examination apparatus 40) corresponding to the counter with each other, and sends them to the management server 10. Further, together with the counter value (and the apparatus ID), the controller 310 may send identification information of the medical institution (medical institution ID) to the management server 10. Incidentally, the medical institution ID is set in advance.

As a first example of a process of transmitting the counter value, the controller 310 may read the counter value indicated by the counter 331 every predetermined time period and control the communication unit 340 to transmit it to the management server 10 together with the apparatus ID. In this example, the management server 10 is notified of the counter value indicating the number of uses of the ophthalmic examination apparatus 40 every predetermined time period. The predetermined time period is, for example, defined in the rental contract. As a typical example, one month is used as the predetermined time period.

As a second example of a process of transmitting the counter value, when the counter value indicated by the counter 331 reaches a predetermined threshold, the controller 310 may control the communication unit 340 to transmit the counter value (or information indicating that the counter value has reached the threshold) to the management server 10 together with the apparatus ID. In this example, the management server 10 is notified of the counter value (or the above information) each time the ophthalmic examination apparatus 40 is used a predetermined number of times. The threshold is, for example, defined in the rental contract and/or in a subsequent operation. In addition, the threshold can be set or changed depending on any factor such as the type of the medical institution (hospital, medical examination center, screening venue, etc.), the scale of the medical institutions, the number of ophthalmic examination apparatuses installed therein, the type of the ophthalmic examination apparatuses, the type of examination to be carried out, and the like.

<Management Server 10>

The management server 10 is an information processing equipment for processing and managing various types of information handled in the management company. The management server 10 has at least a function of performing processes of the embodiment, and may further have any other function. The management server 10 includes one or more information processing equipments. The management server 10 may have a database function to manage information stored in a mass storage device.

The management server 10 includes a controller 110, a communication unit 120, and a storage device 130.

The controller 110 controls each unit of the management server 10. The controller 110 includes a processor and a storage device. The processor performs the control operation according to a computer program stored in the storage device.

The communication unit 120 communicates with other apparatuses via a communication line, a cable, or the like by an arbitrary communication system. For example, the communication unit 120 includes, for example, a communication interface compatible with the Internet, a communication interface compatible with LAN, and a communication interface compatible with near field communication. Data that the communication unit 120 transmits and receives may be encrypted. In this case, the management server 10 (e.g. the controller 110) includes an encryptor that encrypts transmission data and a decoder that decodes received data.

The storage device 130 stores various types of information dealt with in the ophthalmic examination system 1. In particular, the storage device 130 stores the counter value indicated by the counter 331 (and at least one of the medical institution ID and the apparatus ID), which has been transmitted from the medical institution server 30 to the management server 10.

Described below is an example of the configuration of the storage device 130. In the storage device 130, an account (medical institution account) is provided for each medical institution. In addition, each medical institution account is provided with an account (apparatus account) for each of the ophthalmic examination apparatuses 40 installed in the medical institution, or for each predetermined apparatus group including two or more ophthalmic examination apparatuses 40. A variety of information related to the corresponding ophthalmic examination apparatus 40 is recorded on the apparatus account. In particular, each apparatus account is provided with a region (use count recording area) in which the number of uses (the history of the use count) of the corresponding ophthalmic examination apparatus 40 is recorded.

The communication unit 120 receives the information (e.g., medical institution ID, apparatus ID, and counter value) sent from the medical institution server 30, and sends it to the controller 110. The controller 110 identifies the medical institution account corresponding to the medical institution ID, and further, specifies an apparatus account corresponding to the apparatus ID. Then, the controller 110 records the counter value in the use count recording area of the apparatus account specified. At this time, the date and time of transmission or receipt of the information, or the date and time of recording thereof are recorded together with the counter value. Thereby, the use count is recorded for each of the ophthalmic examination apparatuses 40, or each predetermined apparatus group including two or more ophthalmic examination apparatuses 40, and the history is accumulated. With the management server 10, information (e.g., the numbers of uses) related to a plurality of ophthalmic examination apparatuses 40 installed in a plurality of medical institutions can be centrally managed.

<Usage Mode>

Figure 3:
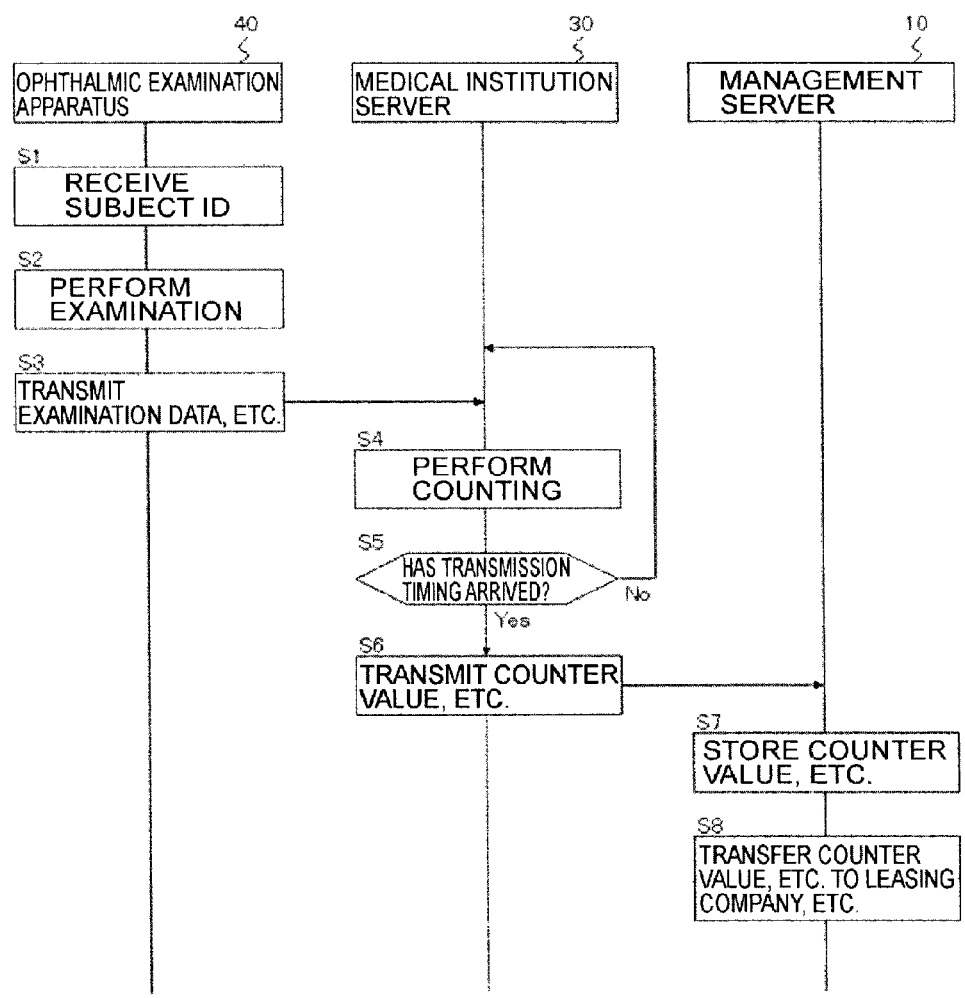
FIG. 3 is a sequence diagram illustrating an example of a usage mode according to an embodiment.

The usage mode of the ophthalmic examination system 1 is described. FIG. 3 illustrates an example of the usage mode for managing the number of times of use of the ophthalmic examination apparatus 40.

(S1: Receive Subject ID)

First, the ID receiver 430 of the ophthalmic examination apparatus 40 receives the subject ID. The subject ID received is sent to the controller 410 and stored therein (temporarily).

(S2: Perform Examination)

Next, the examination unit 420 of the ophthalmic examination apparatus 40 performs the examination of the subject's eye (left eye, right eye, or both eyes). Data obtained by the examination (examination data) is sent to the controller 410.

(S3: Transmit Examination Data, etc.)

The controller 410 associates the subject ID received in step S1, the examination data obtained in step S2, and the apparatus ID stored therein in advance with one another. Then, the communication unit 440 of the ophthalmic examination apparatus 40 transmits the examination data, the apparatus ID, and the subject ID associated with one another to the medical institution server 30.

(S4: Perform Counting)

The communication unit 340 of the medical institution server 30 receives the information sent from the ophthalmic examination apparatus 40 in step S3. The information received is sent to the controller 310. The controller 310 sends at least part of the information to the counting unit 330. The counting unit 330, for example, specifies a counter corresponding to the apparatus ID from among a plurality of counters included in the counter 331, and increases the value of the counter by one unit. Alternatively, the counting unit 330 may perform any of the counting processes described above (e.g., one or more of the first to third examples).

(S5: Has Transmission Timing Arrived?)

In this usage mode, the above process is repeated until the timing of transmitting the counter value to the management server 10 arrives (No in step S5). In other words, each time the examination is performed, the ophthalmic examination apparatus 40 sends a subject ID, examination data, and an apparatus ID to the medical institution server 30, and the medical institution server 30 performs counting based on the information received from the ophthalmic examination apparatus 40.

On the other hand, when the timing of transmitting the counter value to the management server 10 has arrived (Yes in step S5), the process proceeds to step S6.

Incidentally, the transmission timing of the counter value may be set in advance, and the arrival thereof may be determined by the timer function, calendar function, or the like of the controller 310. For example, the controller 310 may be configured to recognize a specific day in every month (the end of the month, etc.) through the calendar function.

Alternatively, the arrival of the transmission timing may be detected by monitoring the counter 331. For example, by monitoring one or more counter values included in the counter 331, the transmission of the counter value may be performed when any of the counter values has reached the threshold. The transmission of the counter value may also be performed when the counter value has reached the threshold in a predetermined number of counters.

The configuration to detect the arrival of the transmission timing by using the timer function and the calendar function may also be combined with the configuration to detect the arrival of the transmission timing by monitoring the counter 331. With this, in addition to periodic notification of the counter value, irregular notification can be provided by the monitoring of the counter 331.

(S6: Transmit Counter Value, etc.)

When the transmission timing of the counter value has arrived (Yes in step S5), the controller 310 reads the counter value from the counter corresponding to each of the ophthalmic examination apparatuses 40 included in the counting unit 330, and associates it with an apparatus ID corresponding thereto. Then, the controller 310 transmits the medical institution ID, and the counter value and the apparatus ID corresponding to each of the ophthalmic examination apparatuses 40 to the management server 10.

(S7: Store Counter Value, etc.)

The communication unit 120 of the management server 10 receives the information sent from the medical institution server 30 in step S6. The information received is sent to the controller 110. The controller 110 stores at least part of the information in the storage device 130. Typically, the controller 110 specifies a medical institution account corresponding to the medical institution ID as well as an apparatus account corresponding to the apparatus ID, and records the counter value and the date and time in the use count recording area of the apparatus account.

(S8: Transfer Counter Value, etc. to Leasing Company, etc.)

The management server 10 may transfer information (including the counter value indicating the number of uses of the ophthalmic examination apparatus 40) collected from a plurality of medical institutions as described above to an external device. This transfer process is performed regularly or irregularly. The destination of the transferred information may include a leasing company server 50.

Part or all of the information stored in the account of each medical institution (including at least the counter value) is transferred to the leasing company server 50 together with the medical institution ID. Thereby, the leasing company can acquire the number of uses of the ophthalmic examination apparatus 40 installed in each medical institution. This allows proper usage-based billing based on the use count of the ophthalmic examination apparatus 40. In other words, the leasing company can charge each medical institution a fee according to the number of uses (counter value) of one or more ophthalmic examination apparatuses 40 installed therein. In addition, the leasing company can calculate the amount of payment to the interpretation center, where the interpretation of an image has been performed at the request of the medical institution, based on the counter value and the like. Further, the leasing company can calculate the amount of the maintenance fee to be paid to the management company (the manufacturer of the ophthalmic examination apparatus 40, the maintenance company thereof, etc.) based on the counter value and the like.

<Embodiment for Assessing the Risk of Disease Using the Ophthalmic Examination Apparatus>

Figure 4:
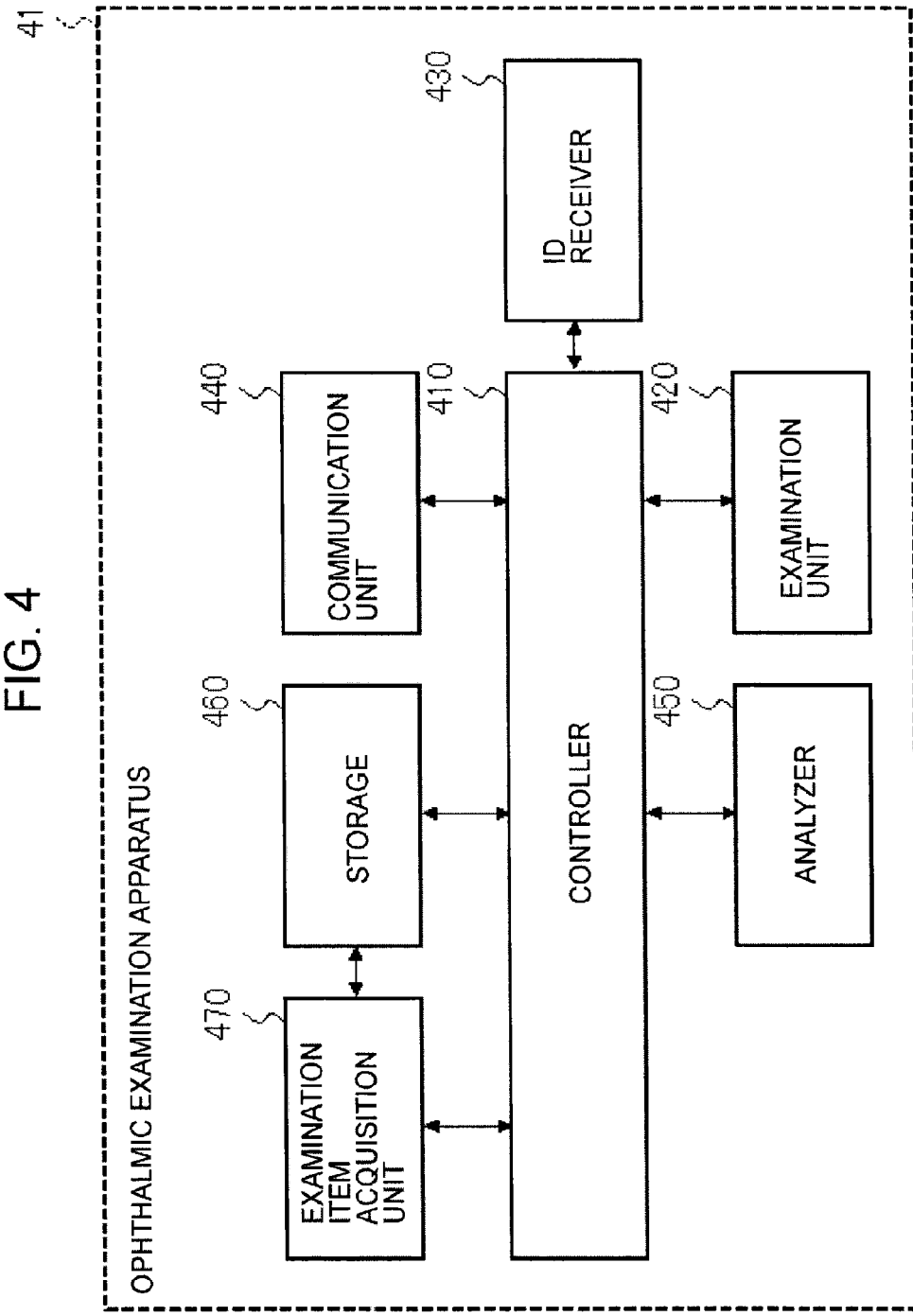
FIG. 4 is a schematic diagram illustrating an example of a configuration according to an embodiment.

A description is given of an ophthalmic examination apparatus of an embodiment having a function for assessing the risk of disease. FIG. 4 illustrates an example of the configuration of the ophthalmic examination apparatus of the embodiment. As illustrated in FIG. 4, an ophthalmic examination apparatus 41 includes the controller 410, the examination unit 420, the ID receiver 430, the communication unit 440, an analyzer 450, a storage 460, and an examination item acquisition unit 470. The controller 410, the examination unit 420, the ID receiver 430, and the communication unit 440 are configured similarly to those described above in connection with FIG. 2.

The analyzer 450 analyzes the examination data obtained by the examination unit 420, and generates risk information indicating the risk of one or more specific diseases. The analyzer 450 includes a processor and a storage device. The processor performs an analysis according to computer programs stored in the storage device.

The term "specific disease" as used herein may refer to any disease, signs of the onset of which or a change in form and/or function that indicates it (lesion) can be detected by ophthalmic examination. Examples of the specific disease include at least one of diabetes, cancer, Alzheimer's disease, hypertension, and arteriosclerosis. Further, the term "risk" indicates the potential of developing the specific disease, and is represented by any parameter (risk information). The risk information includes, for example, a parameter indicating a degree of occurrence of diseases that corresponds to the presence or extent of lesions indicating the symptoms of the disease or the onset thereof. The value of the parameter may be obtained statistically or theoretically, for example.

When the examination data obtained by the examination unit 420 includes image data, the analyzer 450 performs a predetermined image analysis on the image data. In a typical example, the analysis of the image data is performed to obtain parameters representing the form (shape, curvature, thickness, area, volume, position, distribution, etc.) of eye tissue (one or more layers of the cornea, one or more layers of the retina, etc.). It is also possible to obtain the dynamics of the liquid in the eye from the image data. For example, a parameter (blood flow rate, blood flow volume, etc.) related to the blood flowing in the fundus blood vessel and a parameter (circulation rate, circulating volume, distribution, etc.) related to intraocular fluid (aqueous humor) can be obtained from the image data.

At least one of the above parameters can be obtained by, for example, analyzing the image data of the subject's eye (fundus, anterior segment, vitreous, etc.) obtained through OCT scan. Besides, the analysis of an image (enface image, autofluorescence image, etc.) of the retina obtained by fundus photography using a fundus camera or SLO can obtain parameters for the form of the fundus vessel (distribution, diameter, etc.), the presence or extent of lesions, and the presence or degree of a variation in color and/or luminance.

The analyzer 450 may include a normal database created in advance. The normal database may be created by, for example, statistical processing of data collected by examining a plurality of subjects having no specific disease. The normal database represents the range (normal range) of the values of the parameters without the specific disease. The analyzer 450 analyzes the examination data of the subject's eye to obtain a parameter value (analysis data), and determines whether the parameter value falls within the normal range. When the parameter value of the subject's eye falls out of the normal range, the analyzer 450 can determine that the risk of the specific disease is present. Further, the analyzer 450 can obtain the level of risk of the specific disease (risk value) based on the difference between the normal range and the parameter value of the subject's eye. On the other hand, when the parameter value of the subject's eye is in the normal range, the analyzer 450 can determine that there is no risk of the specific disease. Incidentally, if the parameter value of the subject's eye is close to the upper limit or lower limit of the normal range, the analyzer 450 may include information indicating it or information based on it in the risk assessment results.

Similarly, the analyzer 450 may include an abnormal database created in advance. The abnormal database may be created by, for example, statistical processing of data collected by examining a plurality of subjects having the specific disease. The abnormal database represents the range (abnormal range) of the values of the parameters for the specific disease. The analyzer 450 analyzes the examination data of the subject's eye to obtain a parameter value (analysis data), and determines whether the parameter value falls within the abnormal range. When the parameter value of the subject's eye is in the abnormal range, the analyzer 450 can determine that the risk of the specific disease is present.

Further, the analyzer 450 can obtain the level of risk of the specific disease (risk value) based on the abnormal range and the parameter value of the subject's eye. On the other hand, when the parameter value of the subject's eye falls out of the abnormal range, the analyzer 450 can determine that there is no risk of the specific disease. Incidentally, based on the difference between the abnormal range and the parameter value of the subject's eye, the analyzer 450 may include information indicating it or information based on it in the risk assessment results.

The storage 460 stores, in advance, first association information 461 illustrated in FIG. 5A and/or second association information 462 illustrated in FIG. 5B. In the first association information 461, a plurality of diseases A, B, C . . . are each associated with at least one of examination items a, b, c . . . . In the second association information 462, a plurality of risk ranges (default ranges of risk values) set respectively for the diseases A, B, C are each associated with at least one of the examination items a, b, c . . . . Each of the examination items a, b, c . . . represents an item of any medical examination. The medical examination is not limited to the ophthalmic examination. The medical examination may be, for example, an examination used in the screening of higher precision and accuracy compared to the screening using the ophthalmic examination apparatus 41. As a specific example may be cited an examination using a medical image diagnostic apparatus such as X-ray diagnostic apparatus, X-ray CT apparatus, PET apparatus, SPECT apparatus, MRI apparatus, or the like. Further, the medical examination may include laboratory test (sampling) for checking components of a specimen obtained from a human body, the presence of microorganisms, or the like, genetic examination, analysis of biological information (vital signs), and the like.

When the first association information 461 is utilized, the examination item acquisition unit 470 acquires one or more examination items associated with the specific disease indicated by the risk information generated by the analyzer 450 from the first association information 461. For example, having received the risk information generated by the analyzer 450, the examination item acquisition unit 470 specifies the type of disease included in the risk information. When the risk information includes the "disease A", the examination item acquisition unit 470 refers to the first association information 461, and thereby specifies "examination item a", which is an examination item associated with the disease A.

When the second association information 462 is utilized, the examination item acquisition unit 470 specifies one of the risk ranges to which a risk value indicated by the risk information generated by the analyzer 450 belongs, and acquires one or more examination items associated with the risk range from the second association information 462. For example, having received the risk information generated by the analyzer 450, the examination item acquisition unit 470 specifies the type of disease and its risk value included in the risk information. When the risk information includes the "disease A", the examination item acquisition unit 470 determines one of risk ranges "Risk high", "Risk medium" and "Risk low" which includes the risk value of the disease A. Here, these risks ranges are set in advance. The examination item acquisition unit 470 compares each risk range with the risk value of the disease A included in the risk information to specify a risk range to which the risk value belongs. Further, the examination item acquisition unit 470 refers to the first association information 461, and thereby specifies "examination item a", "examination items b" and "examination item c", which are examination items associated with the result of specifying the risk range of the diseases A.

<Usage Mode>

Figure 6:
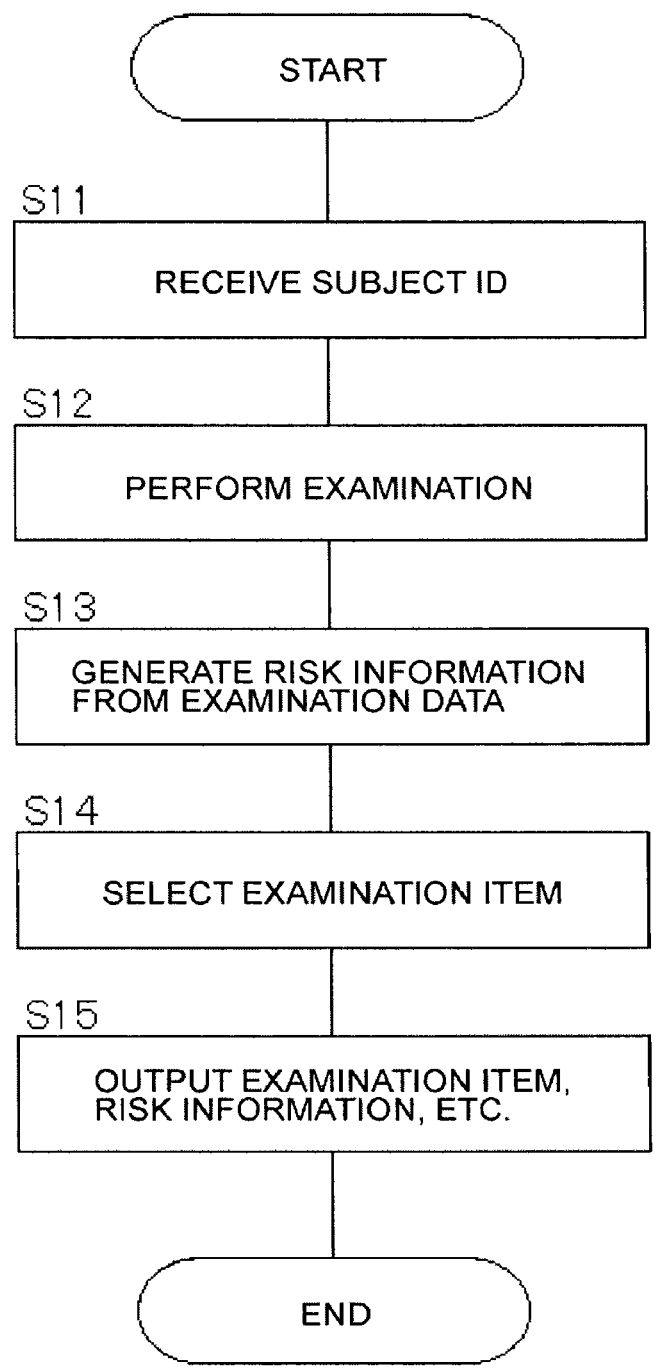
FIG. 6 is a flowchart illustrating an example of a usage mode according to an embodiment.

The usage mode of the ophthalmic examination apparatus 41 is described. FIG. 6 illustrates an example of the usage mode for assessing the risk of disease.

(S11: Receive Subject ID)

First, the ID receiver 430 of the ophthalmic examination apparatus 41 receives the subject ID. The subject ID received is sent to the controller 410 and stored therein (temporarily).

(S12: Perform Examination)

Next, the examination unit 420 of the ophthalmic examination apparatus 41 performs the examination of the subject's eye (left eye, right eye, or both eyes). Data obtained by the examination (examination data) is sent to the controller 410.

(S13: Generate Risk Information from Examination Data)

The controller 410 sends the examination data obtained in step S12 to the analyzer 450. The analyzer 450 analyzes the examination data, and thereby generates risk information. The risk information includes information indicating a disease that is affecting or likely to affect the subject (disease name, etc.), degree of the risk (risk value), or the like. The risk information thus generated is sent to the controller 410.

(S14: Select Examination Item)

The controller 410 sends the risk information generated in step S13 to the examination item acquisition unit 470. The examination item acquisition unit 470 refers to the first association information 461 and/or the second associated information 462 stored in the storage 460 to select one or more examination items associated with the disease name, the risk value, or the like included in the risk information. The examination item acquisition unit 470 sends the examination item(s) thus selected or information indicating the examination item(s) to the controller 410.

(S15: Output Examination Item, Risk Information, etc.)

Under the control of the controller 410, the communication unit 440 transmits the subject ID received in step S11, the examination data acquired in step S12, the risk information generated in step S13, and the examination item(s) selected in step S14 to the medical institution server 30.

The medical institution server 30 stores the information received from the ophthalmic examination apparatus 41. Information obtained for each subject in this way is, for example, printed or transferred. The doctor or the like can explain the risk of the disease and detailed screening (menu of further examination) for the subject based on the information. In addition, it is possible to create a print or electronic information (e-mail, etc.) that presents information about the risk of the disease and the examination menu for each subject to be provided to the doctor, the subject, the relevant department, and professional medical institutions.

Incidentally, the "output" in step S15 may be in any form for outputting the information from the ophthalmic examination apparatus 41 (or another apparatus such as the medical institution server 30). Typical examples of the "output" include transmission to an external device, printing, recording on a recording medium, and the like.

Figure 7:
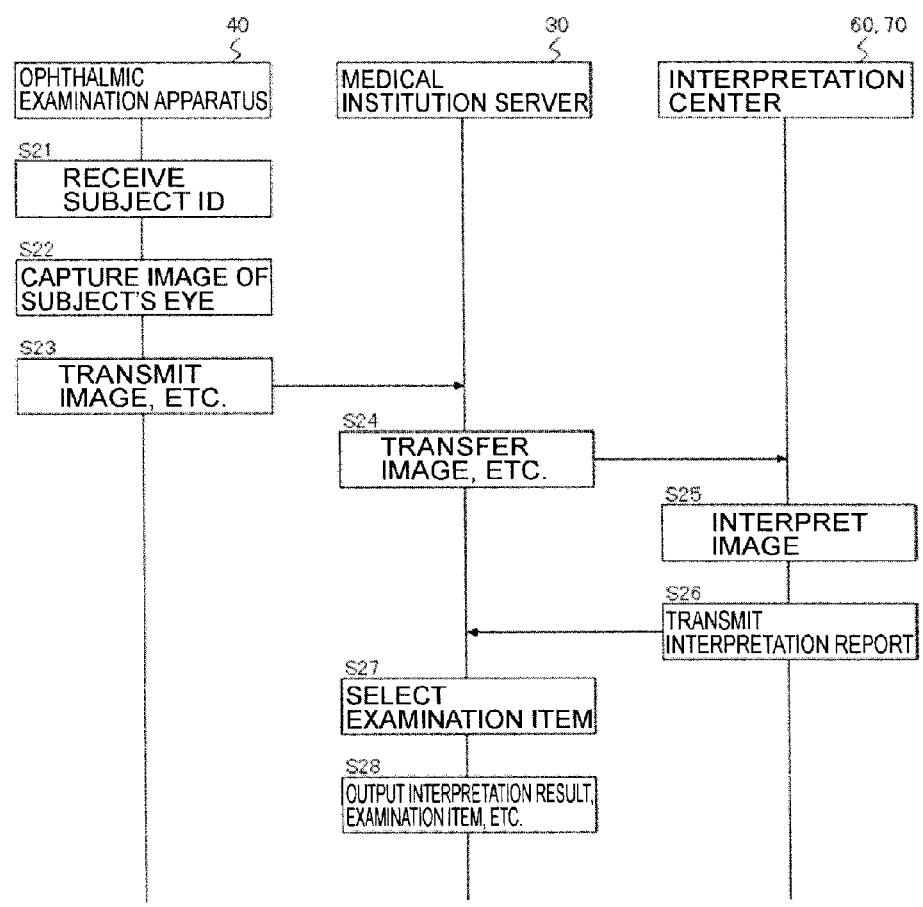
FIG. 7 is a sequence diagram illustrating an example of a usage mode according to an embodiment.

FIG. 7 illustrates another example of the usage mode for assessing the risk of disease. While, in the usage mode illustrated in FIG. 6, the ophthalmic examination apparatus 41 carries out the analysis of the examination data and the creation of examination menu information, these processes may be performed by another apparatus. FIG. 7 illustrates an example of such a usage mode.

If this usage mode is employed, the ophthalmic examination system 1 illustrated in FIG. 1 may have a configuration as follows. First, the ophthalmic examination system 1 is provided with a storage that stores, in advance, association information including the first association information 461 and/or the second association information 462. The storage is provided to, for example, the medical institution server 30. The ophthalmic examination system 1 is also provided with an examination item acquisition unit that acquires, from the association information, an examination item(s) associated with the specific disease included in an interpretation report generated by using the interpretation terminal 70. The examination item acquisition unit has the same configuration as the examination item acquisition unit 470 described above, and is provided to, for example, the medical institution server 30. The ophthalmic examination system 1 is further provided with an output unit that outputs examination menu information including one or more examination items acquired by the examination item acquisition unit. The output unit is provided to, for example, the medical institution server 30.

(S21: Receive Subject ID)

First, the ID receiver 430 of the ophthalmic examination apparatus 40 (or 41) receives the subject ID. The subject ID received is sent to the controller 410 and stored therein (temporarily).

(S22: Capture Image of Subject's Eye)

Next, the examination unit 420 of the ophthalmic examination apparatus 40 captures an image of the subject's eye (left eye, right eye, or both eyes). The examination unit 420 has, for example, OCT function and/or fundus camera function. The image thus captured is sent to the controller 410.

(S23: Transmit Image, etc.)

The controller 410 associates the subject ID received in step S21 with the image captured in step S22. Then, the communication unit 440 of the ophthalmic examination apparatus 40 transmits the subject ID and the image associated with each other to the medical institution server 30.

(S24: Transfer Image, etc.)

The medical institution server 30 transfers the subject ID (or identification information newly assigned) and the image sent from the ophthalmic examination apparatus 40 in step S23 to the interpretation center server 60. The interpretation center server 60 transmits the image received to any of the interpretation terminals 70.

(S25: Interpret Image)

The interpretation terminal 70 includes a user interface (GUI, etc.) for the interpretation of the image. The doctor (ophthalmologist, radiologist, etc.) interprets the image by using the user interface, and creates an interpretation report that includes the results of the interpretation. The interpretation report thus created is sent to the interpretation center server 60.

(S26: Transmit Interpretation Report)

The interpretation center server 60 sends the interpretation report created in the step S25 to the medical institution server 30 together with the subject ID (or the new ID).

(S27: Select Examination Item)

Having received the interpretation report and the like sent from the interpretation center server 60 in step S26, the medical institution server 30 sends it to the examination item acquisition unit. The examination item acquisition unit determines whether the name or the like of any of specific diseases included in the aforementioned association information is described in the interpretation report. If the name or the like of any specific disease is described in the interpretation report, the examination item acquisition unit selects one or more examination items associated with at least one of the specific diseases from the association information.

(S28: Output Interpretation Result, Examination Item, etc.)

The medical institution server 30 outputs, for example, the subject ID (or the new ID, etc.) received in step S21, the image of the subject's eye captured in step S22, the interpretation result obtained in step S25 (part or all of the interpretation report), and the examination item(s) selected in step S27. Incidentally, the "output" may be in any form for outputting the information from the medical institution server 30. Typical examples of the "output" include transmission to an external device, printing, recording on a recording medium, and the like.

<Operations and Effects>

Described below is the operations and effects of the ophthalmic examination apparatus and the ophthalmic examination system according to one embodiment.

The ophthalmic examination apparatus (41) of one embodiment includes an examination unit (420) and an analyzer (450). The examination unit is used to optically examine the subject's eye. The analyzer is configured to analyze examination data obtained by the examination unit, and thereby generate risk information indicating the risk of one or more specific diseases.

According to the embodiment, the risk of the specific disease(s) can be assessed from the examination data obtained by optically examining the subject's eye. This solves the problems in the conventional screening such as radiation exposure, the length of the examination time, and high cost. Specifically, the ophthalmic examination apparatus performs an examination using light having energy within the standard, and therefore is more secure than at least the radiation image diagnostic apparatus. Besides, the examination by the ophthalmic examination apparatus takes a few seconds at the longest, and does not require a few to several tens minutes differently from conventional screening modalities. Further, the cost (medical fees) for the ophthalmic examination is at least a single digit, generally several digits, lower than that by the conventional screening modalities. Thus, according to the embodiment, it is possible to broadly offer the screening of various diseases through an ophthalmic examination.

In an embodiment, the ophthalmic examination apparatus may include a first storage (the storage 460), a first acquisition unit (the examination item acquisition unit 470), and a first output unit (the controller 410, the communication unit 440, etc.). The first storage is configured to store, in advance, first association information (461) that associates each of a plurality of specific diseases with one or more examination items. The first acquisition unit is configured to acquire one or more examination items associated with a specific disease(s) indicated by the risk information generated by the analyzer from the first association information. The first output unit is configured to output examination menu information including the examination item(s) acquired by the first acquisition unit.

With this configuration, a disease that the subject is likely to get in the future or a disease that the subject may be suffering from is specified by ophthalmic examination. Thereby, it is possible to provide an examination menu according to the disease specified. Thus, with respect to diseases that can be detected by screening using ophthalmic examination, examination (screening) of higher precision and accuracy can be proposed.

In an embodiment, the ophthalmic examination apparatus may include a second storage (the storage 460), a second acquisition unit (the examination item acquisition unit 470), and a second output unit (the controller 410, the communication unit 440, etc.). The second storage is configured to store, in advance, second association information (462) that associates each of a plurality of risk ranges with one or more examination items. The second acquisition unit is configured to specify a risk range to which a risk value indicated by the risk information generated by the analyzer belongs, and acquire, from the second association information, one or more examination items associated with the risk range specified. The second output unit is configured to output examination menu information including one or more examination items acquired by the second acquisition unit.

With this configuration, the degree of the risk of a disease that the subject is likely to get in the future or a disease that the subject may be suffering from is specified by ophthalmic examination. Thereby, it is possible to provide an examination menu according to the degree of the risk specified. Thus, with respect to diseases that can be detected by screening using ophthalmic examination, examination (screening) of higher precision and accuracy can be proposed.

In an embodiment, the specific diseases, for which risk assessment and examination menu creation are performed, may include at least one of diabetes, cancer, Alzheimer's disease, hypertension, and arteriosclerosis. Further, in the embodiment, the examination unit (420) may include an OCT unit configured to acquire data of the subject's eye using optical coherence tomography. Thus, it is possible to broadly offer advanced screening using OCT.

According to the embodiment, the ophthalmic examination system includes a plurality of ophthalmic examination apparatuses (the ophthalmic examination apparatus 40 and/or the ophthalmic examination apparatus 41), and one or more interpretation terminals (70). Each of the ophthalmic examination apparatuses is configured to acquire an image by optically examining the subject's eye (e.g. with OCT function). The interpretation terminal(s) receives the image of the subject's eye obtained by any of the ophthalmic examination apparatuses, and includes a user interface for performing interpretation of the image. The ophthalmic examination system further includes a third storage, a third acquisition unit, and a third output unit. The third storage, the third acquisition unit, and the third output unit are provided to, for example, the medical institution server 30. In this case, the third storage is included in the storage device of the controller 310. The third acquisition unit is included in the processor of the controller 310. The third output unit is included in the processor of the controller 310, the communication unit 340, and the like. The third storage is configured to store, in advance, association information (e.g., the first association information 461 and/or the second association information 462) that associates each of a plurality of specific diseases with one or more examination items. The third acquisition unit is configured to, when a result of the interpretation of an image obtained by the interpretation terminal includes information on any of the specific diseases, acquire one or more examination items associated with at least one specific disease, information of which is included in the interpretation result, from the association information. The third output unit is configured to output examination menu information including the examination item(s) acquired by the third acquiring unit.

<Other Features>

Some of the features of the embodiment are described below.

The ophthalmic examination system of one embodiment includes a plurality of ophthalmic examination apparatuses (the ophthalmic examination apparatus 40, 41 etc.) and a management apparatus (the management server 10, the medical institution server 30, etc.) that manages the operational status of these ophthalmic examination apparatuses. The ophthalmic examination system further includes a receiver (the ID receiver 430), a counting unit (330), a storage device (130), and a storage controller (the controller 110).

The receiver (the ID receiver 430) is configured to receive first identification information (subject ID) for identifying the subject.

The counting unit (330) includes a counter (331) provided for each of the ophthalmic examination apparatuses (more generally, for each apparatus group including at least one ophthalmic examination apparatus). The counting unit (330) is configured to count the number of times of use of the ophthalmic examination apparatus in units of the first identification information (subject ID) of the subject examined with the ophthalmic examination apparatus.

The storage controller (the controller 110) is provided in the management apparatus (the management server 10). The storage controller is configured to acquire a counter value indicated by the counter (331) from the counting unit (330). The storage controller is further configured to store the counter value acquired and second identification information (apparatus ID) for identifying the ophthalmic examination apparatus (40) in the storage device (130) in association with each other.

As described above, the ophthalmic examination apparatus of the embodiment is configured to count the number of uses of the ophthalmic examination apparatus (more generally, an apparatus group including at least one ophthalmic examination apparatus) in units of the first identification information for identifying the subject. Thus, it is possible to assess the operational status of the ophthalmic examination apparatus according to the current state of the health care and health care system such as a payment system for medical services. This can promote the use of the ophthalmic examination apparatus for the screening of diseases.

In an embodiment, the counting unit (330) may be configured to operate as follows. First, when a subject corresponding to one first identification information (subject ID) is examined first time in a predetermined period, the counting unit increases the counter value of a counter corresponding to an ophthalmic examination apparatus used for the examination (more generally, a counter corresponding to an apparatus group including the ophthalmic examination apparatus) by one unit. Further, when the subject is examined again in the predetermined period with the ophthalmic examination apparatus (including an ophthalmic examination apparatus of the same type, and/or another ophthalmic examination apparatus in the same apparatus group as that used for the first examination), the counting unit leaves the counter value unchanged.

With this configuration, even if the same examination is performed for one subject a plurality of times during a predetermined time period (e.g., one month), the counter for counting the use of the apparatus (related to usage-based billing) is increased by only 1. Such a counting method is in line with the payment system for medical services related to the examination. That is, such a configuration provides a form for assessing the operational status of the ophthalmic examination apparatus according to the current state of the health care and health care system.

In an embodiment, when either one or both eyes of a subject corresponding to one first identification information (subject ID) are examined, the counting unit (330) may increase the counter value of a counter (331) corresponding to an ophthalmic examination apparatus used for the examination (more generally, a counter corresponding to an apparatus group including the ophthalmic examination apparatus) by one unit.

With this configuration, regardless of whether one or both eyes have been examined, the counter for counting the use of the apparatus (related to usage-based billing) is increased by only 1. Such a counting method is in line with the payment system for medical services related to the examination. Thus, this configuration provides a form for assessing the operational status of the ophthalmic examination apparatus according to the current state of the health care and health care system.

In an embodiment, the counting unit (330) may be configured to operate as follows. First, when either one or both eyes of a subject corresponding to one first identification information (subject ID) are examined, the counting unit (330) increases the counter value of a counter (331) corresponding to an ophthalmic examination apparatus used for the examination (more generally, an apparatus group including the ophthalmic examination apparatus) by one unit. Further, when either one or both eyes of the subject are examined again with the ophthalmic examination apparatus (more generally, an ophthalmic examination apparatus in the same apparatus group), the counting unit leaves the counter value unchanged.

With this configuration, even when the examination is redone, the counter for counting the use of the apparatus (related to usage-based billing) is increased by only 1. Such a counting method is in line with the payment system for medical services related to the examination. Thus, this configuration provides a form for assessing the operational status of the ophthalmic examination apparatus according to the current state of the health care and health care system.

The ophthalmic examination system of an embodiment may include a first transmission controller (the controller 310 of the medical institution server 30) configured to transmit a counter value indicated by the counter (331) to the storage controller (the controller 110 of the management server 10) at regular intervals.

With this configuration, it is possible to periodically transmit the use count (counter value) of each ophthalmic examination apparatus (or each apparatus group) collected during a predetermined time period to the management apparatus (the management server 10). This provides a form of the operation of the ophthalmic examination system Further, the ophthalmic examination system of an embodiment may include a second transmission controller (the controller 310 of the medical institution server 30) that, when a counter value indicated by the counter (331) reaches a predetermined threshold, transmits the counter value to the storage controller (the controller 110 of the management server 10).

With this configuration, the management apparatus (the management server 10) can be notified of that the use count of the ophthalmic examination apparatus (or the apparatus group) has reached the predetermined value. This provides a form of the operation of the ophthalmic examination system. Incidentally, this configuration includes a configuration for transmitting information indicating that the counter value has reached the threshold to the storage controller.

In an embodiment, at least part of the plurality of ophthalmic examination apparatuses (40, 41) may include an OCT unit (the examination unit 420) configured to acquire data of the subject's eye using optical coherence tomography (OCT)

With this configuration, it is possible to broadly offer advanced screening using OCT.

The management apparatus of an embodiment includes the above-mentioned counting unit (330), the storage device (130), and the storage controller (110). Incidentally, in the embodiment illustrated in FIGS. 1 to 3, the combination of the management server 10 and the medical institution server 30 is functioning as the management apparatus. It is also possible to constitute the management apparatus by the combination of other information processing equipments or a single information processing equipment.

<Modifications>

The embodiments described above are mere examples for embodying or carrying out the present invention, and therefore susceptible to several modifications and variations (omission, substitution, addition, etc.), all coming within the scope of the invention.

In the above embodiments, a description is given in detail of the case of counting the number of uses of each ophthalmic examination apparatus; however, it may also be possible to count the total number of uses of two or more ophthalmic examination apparatuses. Incidentally, the configuration of the above embodiments and that of the modification may be generalized as a configuration that counts the number of uses of one or more ophthalmic examination apparatuses as one group (apparatus group).

To count the total number of uses of an apparatus group including two or more ophthalmic examination apparatuses, one counter is assigned to each apparatus group. The counter is associated with the apparatus ID of each of the ophthalmic examination apparatuses. Incidentally, the same apparatus ID may be assigned to the ophthalmic examination apparatuses corresponding to one counter. Having received examination data together with a subject ID and an apparatus ID from the ophthalmic examination apparatus, as in the same manner as described in the above embodiments, the counting unit specifies a counter corresponding to the apparatus ID to perform the counting process. The counting process may be, for example, any one or any combination of two or more counting processes described in the above embodiments. Configurations, processing, or the like other than such a counting process may be basically the same as those in the above embodiments. This modification eliminates the need to provide a counter for each of the ophthalmic examination apparatuses to perform counting individually. Thus, the configuration can be simplified.

There are ophthalmic examination apparatuses capable of performing multiple examinations. Examples of such apparatuses include a multifunctional machine combining an optical coherence tomography and a fundus camera. In addition, there are ophthalmic examination apparatuses capable of examining different tissues of the subject's eye. Examples of such apparatuses include an optical coherence tomography that can examine both the fundus and anterior segment of the subject's eye. There are ophthalmic examination apparatuses capable of performing different types of analysis. Examples of such apparatuses include an optical coherence tomography (and an analyzer) that can perform the examination of the optic disc for glaucoma diagnosis as well as the examination of the macula for the diagnosis of age-related macular degeneration.

When an ophthalmic examination apparatus (one or more types of ophthalmic examination apparatuses) capable of performing multiple examinations as above is used, medical fees may vary depending on the type of examination. To cope with this, one unit of the count may be varied depending on the type of examination. In this case, an examination ID indicating the type of examination performed is entered to the counting unit together with a subject ID and an apparatus ID. Alternatively, the counting unit or the like may specify the examination type based on examination data received together with a subject ID and an apparatus ID. The counting unit operates to increase the value of a counter corresponding to the apparatus ID by one unit corresponding to the examination ID (or the examination type). Configurations, processing, or the like other than such a counting process may be basically the same as those in the above embodiments. According to this modification, the number of uses of the ophthalmic examination apparatus can be counted according to the examination type.

In the ophthalmic examination system, the ophthalmic examination apparatuses may include two or more types of ophthalmic examination apparatuses. For example, the ophthalmic examination apparatuses may include one or more optical coherence tomography, one or more SLO, and one or more fundus cameras. In this case, the counting unit may include a counter for each type of the ophthalmic examination apparatuses. Each of the ophthalmic examination apparatuses may be assigned an apparatus ID corresponding to its type. The counting unit performs the count process with a counter for an apparatus of the type corresponding to the apparatus ID. Alternatively, the counting unit may be configured to store, in advance, information that associates the apparatus ID of each ophthalmic examination apparatus with the apparatus type (ID of the counter), and specify a counter corresponding to the apparatus ID in reference to the information to thereby perform the counting process with the counter specified.

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic examination apparatus, comprising: an examination unit used to optically examine a subject's eye; and an analyzer configured to analyze examination data obtained by the examination unit, and thereby generate risk information indicating a risk of a specific disease;

further comprising: a first storage configured to store, in advance, first association, information that associates each of a plurality of specific diseases with one or more examination items; a first acquisition unit configured to acquire one or more examination items associated with a specific disease indicated by the risk information generated by the analyzer from the first association information; and a first output unit configured to output examination menu information including the one or more examination items acquired by the first acquisition unit.

2. The ophthalmic examination apparatus of claim 1, wherein the specific disease includes at least one of diabetes, cancer, Alzheimer's disease, hypertension, and arteriosclerosis.

3. The ophthalmic examination apparatus of claim 1, wherein the examination unit includes an OCT unit configured to acquire data of the subject's eye using optical coherence tomography.

4. An ophthalmic examination apparatus, comprising:
an examination unit used to optically examine a subject's eye;
an analyzer configured to analyze examination data obtained by the examination unit, and thereby generate risk information indicating a risk of a specific disease,
a second storage configured to store, in advance, second association information that associates each of a plurality of risk ranges with one or more examination items;
a second acquisition unit configured to specify a risk range from the risk ranges to which a risk value indicated by the risk information generated by the analyzer belongs, and acquire one or more examination items associated with the specified risk range from the second association information; and
a second output unit configured to output examination menu information including the one or more examination items acquired by the second acquisition unit.

5. The ophthalmic examination apparatus of claim 4, further comprising:
a first storage configured to store, in advance, first association information that associates each of a plurality of specific diseases with one or more examination items;
a first acquisition unit configured to acquire one or more examination items associated with a specific disease indicated by the risk information generated by the analyzer from the first association information; and
a first output unit configured to output examination menu information including the one or more examination items acquired by the first acquisition unit.

6. The ophthalmic examination apparatus of claim 4, wherein the specific disease includes at least one of diabetes, cancer, Alzheimer's disease, hypertension, and arteriosclerosis.

7. The ophthalmic examination apparatus of claim 4, wherein the examination unit includes an OCT unit configured to acquire data of the subject's eye using optical coherence tomography.

8. An ophthalmic examination system, comprising:
a plurality of ophthalmic examination apparatuses each configured to acquire an image by optically examining a subject's eye; and
at least one interpretation terminal each configured to receive the image of the subject's eye obtained by any of the ophthalmic examination apparatuses, and each including a user interface to interpret the image,
wherein the ophthalmic examination system comprises:
a third storage configured to store, in advance, association information that associates each of a plurality of specific diseases with one or more examination items;
a third acquisition unit configured to, when an interpretation result of the image generated by using the interpretation terminal includes information on any of the specific diseases, acquire one or more examination items associated with at least one specific disease, information of which is included in the interpretation result, from the association information; and
a third output unit configured to output examination menu information including the one or more examination items acquired by the third acquiring unit.

* * * * *